United States Patent [19]

Spaulding et al.

[11] Patent Number: 4,867,898
[45] Date of Patent: Sep. 19, 1989

[54] BROAD SPECTRUM ANTIMICROBIAL SYSTEM FOR HARD SURFACE CLEANERS

[75] Inventors: Laura Spaulding, Wayne; Arthur Rebarber, Elmwood Park; Eugene Wiese, Hopatcong, all of N.J.

[73] Assignee: American Cyanamid Company, Stamford, Conn.

[21] Appl. No.: 28,814

[22] Filed: Mar. 23, 1987

[51] Int. Cl.⁴ ............................ C11D 7/44; C11D 3/48
[52] U.S. Cl. ..................................... 252/106; 252/142; 252/143; 424/195.1
[58] Field of Search ............... 252/106, 107, 142, 143; 424/195.1

[56] References Cited

U.S. PATENT DOCUMENTS 3,666,668  5/1972  Klausner .............................. 252/106
3,703,472 11/1972  Shaw et al. ......................... 252/107

FOREIGN PATENT DOCUMENTS 1120820  3/1982  Canada .
1153267  9/1983  Canada .
1961516  6/1971  Fed. Rep. of Germany .
  18447  6/1973  Japan .

Primary Examiner—Prince E. Willis
Attorney, Agent, or Firm—Anthony M. Santini; Charles J. Fickey

[57] ABSTRACT

A liquid hard surface cleaner having broad spectrum disinfectancy activity based on a synergistic effect between pine oil and organic, oil soluble acids at a pH of 0 to 6. The cleaner has disinfectancy activity against both gram positive and gram negative organisms.

9 Claims, No Drawings

BROAD SPECTRUM ANTIMICROBIAL SYSTEM FOR HARD SURFACE CLEANERS

This invention relates to a liquid hard surface cleaner having broad spectrum disinfectancy and containing pine oil.

A number of pine oil containing cleaners are known for cleaning hard surfaces, i.e. porcelain, enamel, plastic laminates and the like. Such cleaners are effective for cleaning greasy soil, and in combination with certain surfactants they have been effective in cleaning grimy soil from surfaces. However, pine oil based cleaners have not been found to have broad spectrum antimicrobial activity since they are only effective against gram negative organisms and not against gram positive organisms unless quaternary ammonium compounds are present. The use of quaternary compounds in a cleaner is not desirable since these compounds have a number of undesirable qualities. A high residue is left on the surface after cleaning. In addition, quaternary ammonium compounds are too toxic for this use and are highly irritating to the skin, eyes etc.

It is therefore an object of this invention to provide a pine oil containing hard surface cleaner that has broad spectrum disinfectancy, but does not contain quaternary ammonium compounds.

It has now been found that the above object may be attained by the use of certain organic oil soluble acids in combination with pine oil in a liquid cleaning composition at a pH of 0 to 6. Pine oil is known as an ingredient of liquid cleaners as poined out above.

The organic oil soluble acids used here are benzene carboxylic or hydroxy carboxylic acids, such as benzilic acid, salicyclic acid and phthalic acid; organic straight chain carboxylic or hydroxy carboxylic acids such as sorbic acid, malic acid, malonic acid, glutaric acid, adipic acid, tartaric acid and citric acid and nitrogen containing heterocyclic acids such as picolinic and nicotinic acids. Such acids are well known and widely used, but to our knowledge have not been used as a component of a disinfectant cleaning composition.

The ingredients and amounts that make up the hard surface cleaner of the present invention are lised in Table I below. It will be understood that the listing of oil soluble organic acids and of detergents is exemplary and not inclusive.

TABLE I

CONCENTRATION RANGES OF RAW MATERIAL

| CONCENTRATION | ACTIVE INGREDIENTS |
|---|---|
| 1.00 to 30.00 | Pine Oil |
| 0.05 to 5.00 | Oil soluble acid: Sorbic, Benzoic Salicylic, Phthalic, Benzilic |

| CONCENTRATION | INERT INGREDIENTS |
|---|---|
| 0.10 to 10.00 | Isopropyl Alcohol |
| 0.01 to 2.00 | Fenchyl Alcohol |
| 0.01 to 1.00 | Ammonium Hydroxide |
| 0.01 to 2.00 | Ethylene diamine tetra acetic acid. |

Optionally one or more of the ingredients listed below for effective detergency.

| | |
|---|---|
| 0.10 to 10.00 | Sodium C13–C18 Paraffin Sulfonate |
| 0.10 to 10.00 | Sodium Dodecyl Benzene Sulfonate |
| 0.10 to 10.00 | Polyoxyethylene (8) C9–C11 Ether |
| 0.10 to 10.00 | Sodium C14–C16 Olefin Sulfonate |
| 0.10 to 10.00 | Sodium Pareth-25 Sulfate |
| q.s | Water |
| 100.00% | |

As previously described, pine oil is not effective against gram positive organisms, although it is effective against gram negative organisms. It is, therefore, surprising that a combination of pine oil and an oil soluble organic acid, as described previously, has broad spectrum disinfectancy and is effective against both gram negative and gram positive bacteria at a pH of 0 to 6. We have found that this is a truly synergistic effect since a composition containing pine oil but no oil soluble acids was ineffective against *Staphylococcus aureus* (gram positive). A similar composition containing pine oil but no oil soluble acids was also ineffective against *S. aureus*. However, a similar composition containing both pine oil and oil soluble organic acids at a pH of 0 to 6 was surprisingly found to be 100 percent effective against *S. aureus*. Thus, this composition has broad spectrum disinfectancy since it is effective against both gram positive and gram negative organisms.

The present liquid hard surface cleaner thus has use in hospitals, due to its broad spectrum activity, in industrial use and consumer use. The active ingredients were effective on bacteria grown on either nutrient broth or synthetic media. The composition, according to the invention, gives excellent cleaning on greasy, grimy, fingerprint and soap scum soils. The combination of pine oil and oil soluble organic acids is safe enough for use as a consumer product.

In order to demonstrate the synergistic broad spectrum disinfectancy effect of the cleaner of the present invention, the following specific Examples are set forth:

Example I to III

A formulation (I) according to the present application was prepared with the ingredients and amounts thereof as shown in Table I and having a pH of between 0 and 6. Second formulation (II) was prepared identical to formulation I, except that the oil soluble acid was not included.

A third formulation (III) was prepared identical to formulation I, except that the pine oil was not included.

Example II

Formulations of II and III of Example I were subjected to microbiological testing according to the Association of Official Analytical Chemists-Use Dilution Method (AOAC-UDM) procedure as used by the Environmental Protective Agency (EPA) and industry in general, against *S. aureus*. The results are shown in Table II.

TABLE II

GRAM POSITIVE MICROBIOLOGICAL ACTIVITY OF CLEANERS

| ACTIVE INGREDIENT | S. AUREUS* |
|---|---|
| FORMULA II - PINE OIL | 0-/60 |
| FORMULA IIIA - SORBIC ACID | 0-/20 |
| FORMULA IIIB - BENZOIC ACID | 0-/20 |

*Accomplished according to the AOAC-UDM procedure

Example III

A number of Examples of Formulation I of Example I were submitted to microbiological testing against *Staphylococcus aureus*\* (synthetic, nutrient), *Salmonella choleraesuis*\* (synthetic nutrient), *Pseudomonas aeruginosa*\* (nutrient) and *Escherichia coli*\* (nutrient). The results are shown in Tables III and IV. It will be seen that these formulations have disinfectancy activity against both gram positive and gram negative organisms and thus broad spectrum disinfectancy:

\**S. aureus*-gram positive
*S. choleraesuis*-gram negative
*P. aeruginosa*-gram negative
*E. coli*-gram negative

TABLE III

GRAM POSITIVE MICROBIOLOGICAL ACTIVITY OF PINE/OIL-SOLUBLE ACID BLENDS

| ACTIVE INGREDIENTS | S. AUREUS* |
|---|---|
| Pine Oil + Sorbic Acid | 59-/60 |
| Pine Oil + Benzoic Acid | 60-/60 |
| Pine Oil + Phthallic Acid | 59-/60 |
| Pine Oil + Benzilic Acid | 60-/60 |
| Pine Oil + Salicylic Acid | 20-/20 |

\*Accomplished according to the AOAC-UDM procedure, which allows for one failure in a 60 tube test.

TABLE IV

BROAD SPECTRUM ANTIMICROBIAL ACTIVITY OF A BENZOIC ACID/PINE OIL COMPOSITION

| ORGANISM | MEDIA | RESULT* |
|---|---|---|
| S. aureus | synthetic | 60-/60 |
| S. aureus | nutrient | 59-/60 |
| S. choleraesuis | synthetic | 59-/60 |
| S. choleraesuis | nutrient | 60-/60 |
| P. aeruginosa | nutrient | 60-/60 |
| E. coli | nutrient | 10-/10 |

\*Accomplished according to the AOAC-UDM procedure, which allows for one failure in a 60 tube test.

It will be seen that the combination of pine oil and oil soluble organic acids has a clear, and surprising synergistic effect in providing disinfectancy activity against both gram positive and gram negative organisms and that a liquid cleaner is provided for hard surfaces having a broad sepctrum activity.

What is claimed is:

1. A liquid cleaner for hard surfaces having broad spectrum disinfectancy activty comprising antimicrobial effective amounts of pine oil and at least one oil soluble organic acid said composition having a pH of 0 to 6.

2. The cleaner of claim 1 wherein the oil soluble organic acid is selected from the group consisting of benzilic acid, benzoic acid, salicyclic acid, phthalic acid, sorbic acid, malic acid, malonic acid, glutaric acid, adipic acid, tartaric acid, picolinic acid and nicotinic acid.

3. The cleaner of claim 1 further comprising organic detergent compounds.

4. The cleaner of claim 3 further comprising isopropyl alcohol.

5. The cleaner of claim 3 further comprising fenchyl alcohol.

6. The cleaner of claim 3 further comprising ammonium hydroxide.

7. The cleaner of claim 3 further comprising ethylene diamene tetra acetic acid.

8. A method of imparting broad spectrum disinfectant activity to a hard surface comprising applying to said surface a liquid cleaner composition said composition comprising antimicrobial effective amounts of pine oil and at least one oil soluble organic acid said composition having a pH of 0 to 6.

9. The method of claim 8 wherein the oil soluble organic acid is selected from the group consisting of benzilic acid, benzoic acid, salicyclic acid, phthalic acid, sorbic acid, malic acid, malonic acid, glutaric acid, adipic acid, tartaric acid, picolinic acid and nicotinic acid.

* * * * *